United States Patent
Vasta et al.

(10) Patent No.: US 8,430,878 B2
(45) Date of Patent: Apr. 30, 2013

(54) ADJUSTABLE ORTHOPEDIC FIXATION SYSTEM

(75) Inventors: Paul Vasta, McKinney, TX (US); David Crook, Mineola, TX (US); Michael Thomas, Van Alstyne, TX (US)

(73) Assignee: AMEI Technologies, Inc., Wilmington, DE (US)

( * ) Notice: Subject to any disclaimer, the term of this patent is extended or adjusted under 35 U.S.C. 154(b) by 219 days.

(21) Appl. No.: 12/618,514

(22) Filed: Nov. 13, 2009

(65) Prior Publication Data

US 2011/0118738 A1   May 19, 2011

(51) Int. Cl.
*A61B 17/62* (2006.01)

(52) U.S. Cl.
USPC .............................................. 606/56

(58) Field of Classification Search .............. 606/53–60
See application file for complete search history.

(56) References Cited

U.S. PATENT DOCUMENTS

| | | | |
|---|---|---|---|
| 4,365,624 A | 12/1982 | Jaquet | |
| 4,988,244 A * | 1/1991 | Sheldon et al. | 409/132 |
| 5,095,919 A | 3/1992 | Monticelli et al. | |
| 5,533,418 A | 7/1996 | Wu et al. | |
| 5,776,132 A | 7/1998 | Blyakher | |
| 5,891,143 A | 4/1999 | Taylor et al. | |
| 6,030,386 A | 2/2000 | Taylor et al. | |
| 2002/0010465 A1* | 1/2002 | Koo et al. | 606/57 |
| 2005/0215997 A1 | 9/2005 | Austin et al. | |
| 2007/0055234 A1 | 3/2007 | McGrath et al. | |
| 2009/0036890 A1 | 2/2009 | Karidis | |

OTHER PUBLICATIONS

International Search Report of corresponding PCT application No. PCT/US2010/056539 dated Jan. 18, 2011.
International Preliminary Report on Patentability, PCT/US2010/056539, international filing date Nov. 12, 2010, date of issuance of report May 15, 2012, 9 pages.
International Preliminary Report on Patentability, PCT/US2010/056541, international filing date Nov. 12, 2010, date of issuance of report May 15, 2012, 7 pages.
International Search Report, PCT/US2010/056541, date of mailing Jan. 12, 2011, 2 pages.

* cited by examiner

*Primary Examiner* — Jan Christopher Merene
*Assistant Examiner* — Jerry Cumberledge
(74) *Attorney, Agent, or Firm* — Baker & McKenzie LLP (57) ABSTRACT

An orthopedic fixation system having two rings or other base/frame elements separated by a plurality of struts. The struts are attached to the rings by a combination of a attachment mechanism having at least two degrees of movement each, and at least one connecting mechanism. The connecting mechanisms may be moveably or non-moveably connected to one or more tracks located on either or both rings of base elements. A combination of these elements provides a fixation device that allows for six degrees of freedom of movement between the rings or other base elements.

50 Claims, 6 Drawing Sheets

ADJUSTABLE ORTHOPEDIC FIXATION SYSTEM

TECHNICAL FIELD

The present disclosure relates to orthopedic fixation systems, more particularly to improved orthopedic fixation systems that use a plurality of rigid struts of equal or non-equal length to support a pair of base members, such as rings affixed to respective bone parts with pins.

BACKGROUND

Without limiting the scope of the present disclosure, this background is described in connection with external fixation devices. Generally, external fixation devices are commonly used on both the upper and lower limbs for both adults and children in a variety of surgical procedures including limb lengthening, deformity correction and treatment of fractures, mal-unions, non-unions and bone defects. Such orthopedic fixation systems may be utilized to treat fractures of the skeleton, soft tissue injuries, delayed union of the skeleton when bones are slow to heal, nonunion of the skeleton when bones have not healed, mal-union where broken or fractured bones have healed in a mal-position, congenital deformities where bones develop a mal-position, and bone lengthening, widening, or twisting. These systems are sometimes called "halo" systems or "hexapod" type circular ring fixation systems.

Such ring-based fixator systems are typically placed on the affected patient by medical personnel in such a way as to align the affected body part during the healing process, holding the affected body part in the proper position for treatment. For example, such fixators may be used to stabilize bone fragments by holding the fragments in a relatively fixed spatial relation, and are adjustable orthopedic systems that allow the physician or other medical professional to reorient one fragment with respect to another along all six axes in an acute motion, usually by loosening one or more clamps and effecting the corrective motion manually and then retightening clamps to stably hold the fragments in the desired position. Since applications of such devices can include a wide variety of deformities, body sites, and surgical implementations, there is a need for fixation devices that can initially be acutely adjusted in order to accommodate such variabilities, and subsequently maintain the affected body part in one desirable position. Moreover, a typical treatment regimen requires frequent adjustments to be performed by the patient and/or during repeated visits to medical professionals so that the fixation device can be periodically and gradually adjusted, providing the desired orientation to the affected body part and setting the proper amount of support and stretching or compression for healing.

One common external fixation device of type discussed above is known as the Ilizarov apparatus. The Ilizarov external fixation procedure involves a rigid framework consisting of several rings or arches that are placed externally around the limb, and attached to injured (e.g., due to fracture) or surgically separated (e.g., for limb lengthening and deformity correction) bone segments using special bone fasteners (wires and pins) inserted into the bone segment and connected to the related section of the external rigid framework.

Another common external fixation device of the type discussed above is a Taylor Spatial Frame, as described in U.S. Pat. Nos. 6,030,386, 5,891,143, and 5,776,132. The Taylor Spatial Frame is a hexapod-type of device and shares many components and features of the Ilizarov apparatus. The Taylor Spatial Frame consists of two external fixator rings attached to bone segments by wires or half-pins, and connected together by six struts that may be lengthened or shortened as necessary. Adjustment of strut lengths allows manipulation of the bone segments in 6 axes (e.g., lengthening/shortening, external/internal rotation, anterior/posterior horizontal translation, medial/lateral horizontal translation, anterior/posterior angular translation, and medial/lateral angular translation) to correct linear, angular and rotational deformities simultaneously.

Looking specifically into their functionality, with most fixators based on rings or arches like those discussed above, the opposite rings/frames of the rigid framework are connected by either threaded or telescopic connection rods or by assembled uni-planar or multi-planar angular hinges, which allow the medical professional to adjust the relative position of the rings to each other longitudinally or angularly over a period of time. This allows new bone to gradually form in the gap between bone segments created by this distraction technique. Once the desired position of bone segments is achieved over the course of time (e.g., 2-6 weeks), the external apparatus is stabilized into a fixed position and left on the bone segments until the fracture is healed or newly formed bone is completely or substantially mineralized, which could take up to an additional 3-6 months, depending on the nature of pathology and degree of deformity.

Based on the above, current orthopedic fixation systems may have a number of mechanical benefits, including flexibility in positioning one ring with respect to another, and strength during compressive loading. However, configurations that can provide a full six degrees of freedom between two circular fixator rings typically require adding struts to increase range of movement, which is problematic from a clinical use perspective, or require having fewer struts, which requires multiple degrees of controllable motion within each strut and thereby unfortunately reducing the overall system strength in supporting loads. Accordingly, an orthopedic ring fixation system is needed that provides six degrees of freedom, but that is easy to configure and does not reduce the overall system strength. Still other objects and advantages of the invention will become clear upon review of the following detailed description in conjunction with the appended drawings.

SUMMARY

Disclosed herein are improved orthopedic fixation systems that use a plurality of rigid struts, typically of equal or unequal length, to support a pair of base members, such as rings affixed to respective bone parts with pins. The orthopedic fixation systems can comprise two rings separated by the plurality of struts. The one or more of the struts are attached to the rings by a combination of a moveable attachment mechanism and a slidable connecting mechanism. The slidable connecting mechanisms are connected to and slide along one or more tracks located on the two base elements, which allows for six degrees of freedom of movement between the base elements.

In one embodiment, an orthopedic fixation system may comprise a first base element comprising at least one track located on at least a portion of the perimeter of the first base element, and a second base element comprising at least one track located on at least a portion of the perimeter of the second base element. This embodiment of the system may also comprise at least six rigid struts spanning between the first base element and the second base element, each of the struts comprising an upper attachment mechanism and a lower attachment mechanism on opposite ends, where the attachment mechanisms are each capable of at least two degrees of movement. In addition, the system may comprise one or more upper connecting mechanisms for moveably connecting one or more corresponding ones of the upper attachment mechanisms to the track of the first base element, as well as one or more lower connecting mechanisms for moveably connecting one or more corresponding ones of the lower attachment mechanisms to the track of the second base element.

In another embodiment, an orthopedic fixation system may comprise an upper ring comprising at least one circumferential track and six upper connecting members which are moveable around the at least one track, and a lower ring comprising at least one circumferential track and six lower connecting members which are moveable around the at least one track. In such an embodiment, the system may also comprise at least six struts, each strut comprising a rigid rod, an upper attachment member having at least two degrees of movement at one end, and a lower attachment member having at least two degrees of movement at an opposing end. In these embodiments, each upper attachment member is connected to a corresponding one of the upper connecting members, and each lower attachment member is connected to a corresponding one of the lower connecting members.

In yet another embodiment, an orthopedic fixation system may comprise an upper ring comprising a first circumferential track having at least three first upper connecting members, one or more of which are moveable around the first track, and a second circumferential track having at least three second upper connecting members, one or more of which are moveable around the second track. The fixation system may also comprise a lower ring comprising a third circumferential track having at least three first lower connecting members, one or more of which are moveable around the third track, and a fourth circumferential track having at least three second lower connecting members, one or more of which are moveable around the fourth track. The system may further comprise at least six struts, each strut comprising a rigid rod, an upper attachment member having at least two degrees of movement at one end, and a lower attachment member having at least two degrees of movement at an opposing end. In such embodiments, the at least three upper attachment members on the first track are connected to corresponding ones of the at least three first upper connecting members, and the at least three upper attachment members on the second track are connected to corresponding ones of the at least three second upper connecting members. Furthermore, the at least three lower attachment members on the third track are connected to corresponding ones of the at least three first lower connecting members, and wherein the at least three lower attachment members on the fourth track are connected to corresponding ones of the at least three second lower connecting members.

In yet a further embodiment, an orthopedic fixation system constructed according to the disclosed principles may comprise a first base element and a second base element, at least one of the first or second base elements comprising at least one track located on at least a portion of the perimeter of the first base element. Such a system may also comprise a plurality of rigid struts spanning between the first and second base elements, each of the struts comprising an upper attachment mechanism and a lower attachment mechanism on opposite ends, where the attachment mechanisms are each capable of at least two degrees of movement. Such embodiments may further comprise one or more upper connecting mechanisms for connecting one or more corresponding ones of the upper attachment mechanisms to the track of the first base element, and one or more lower connecting mechanisms for connecting one or more corresponding ones of the lower attachment mechanisms to the track of the second base element. In these embodiments, at least one of the upper and lower connecting mechanisms is moveable along a corresponding one of the at least one track.

BRIEF DESCRIPTION OF THE DRAWINGS

For a more complete understanding of the features and advantages of the present disclosure, reference is now made to the detailed description along with the accompanying figures and in which.

DETAILED DESCRIPTION

The following detailed description is of the best mode or modes of the invention or inventions presently contemplated. Such description is not intended to be understood in a limiting sense, but to be an example of the invention presented solely for illustration thereof, and by reference to which in connection with the following description and the accompanying drawings one skilled in the art may be advised of the advantages and construction of the invention. The invention is intended to cover alternatives, modifications, and equivalents, which may be included within the spirit and scope of the invention as defined by the appended claims.

Figure 1:
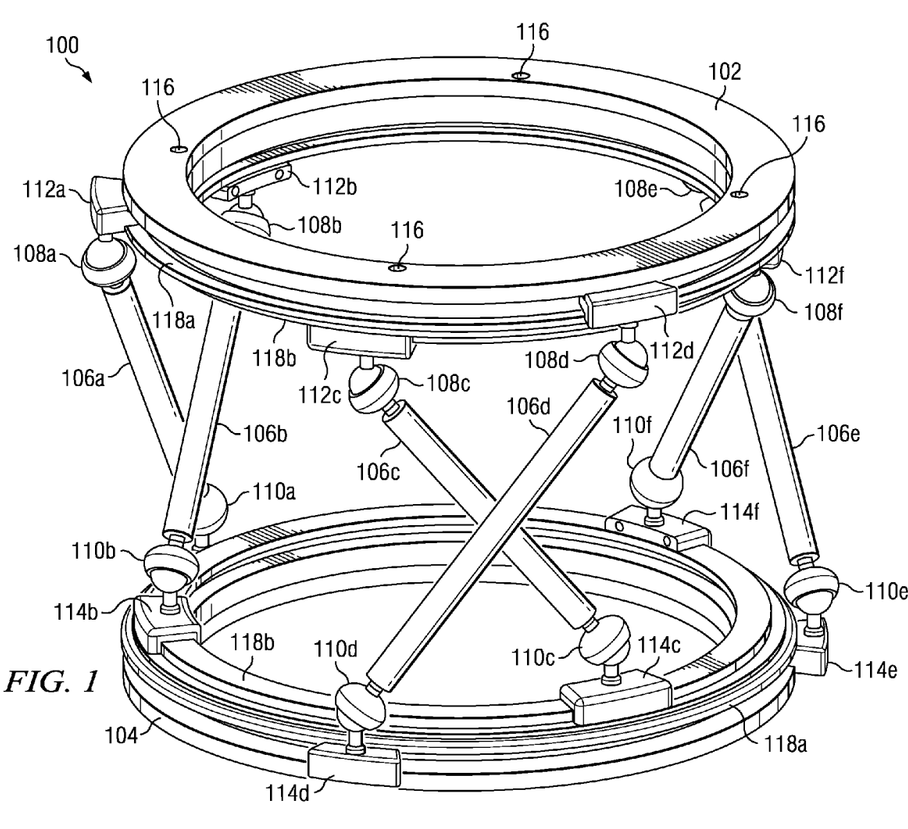
FIG. 1 is a perspective view of an embodiment of an orthopedic fixation system of the present invention.
Figure 1A:
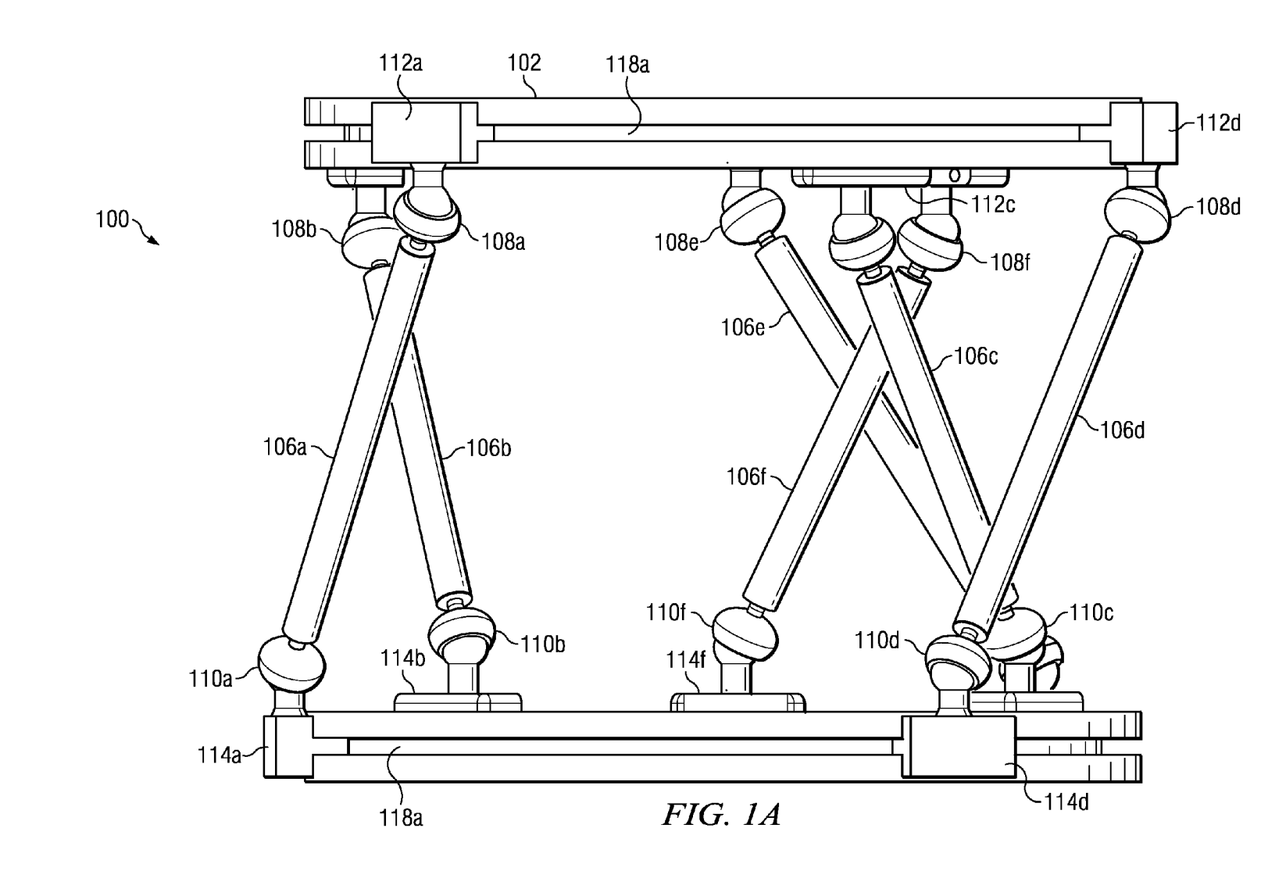
FIG. 1A is a side view of the embodiment of the orthopedic fixation system of FIG. 1.

An embodiment of an orthopedic fixation system is shown in FIG. 1 and identified by the numeral 100. The orthopedic fixation system 100 includes a first base element 102 and a second base element 104. The first base element 102 and the second base element 104 are preferably spaced apart by a plurality of struts 106a-106f. Although six struts 106 of substantially equal length are illustrated, none of the embodiments of a fixator device constructed as disclosed herein is limited to specifically six struts 106, nor is there any limitation to the use of all equal length struts 106. In fact, in some applications, the fixator device 100 may specifically require struts 106 of unequal length for proper implementation. In addition, although only two base elements 102, 104 are illustrated and described below, it should be understood that 3 or more base elements may also be employed with the principles of the present disclosure disclosed herein. Moreover, although such base elements are often discussed herein as "rings," it should be understood that an entirely circular shape for the elements is not necessarily intended. Also, the elements may comprise only partially enclosed fixator elements, such as only a partial circular structure.

Furthermore, elements in the accompanying drawings that are the same except for their location have been given the same number but a different alphabetic character. For example, a first strut is 106a, a second strut 106b, etc. If there are a plurality of the same element, then only one such element is described and all such elements are deemed identical.

Moreover, the materials of all parts/components described herein may be those materials typically used in orthopedic instruments and known to those skilled in the art, for example, but not limited to, stainless steel, fiberglass, titanium, etc. In advantageous embodiments, some or all of the materials may be constructed from radiotranslucent materials, to aid in the x-raying of the afflicted area being treated by the fixator 100. Of course, no limitation to any particular material is intended or should be implied.

Struts 106 include an upper attachment mechanism 108a-108f and a lower attachment mechanism 110a-110f. Each upper attachment mechanism 108 is mounted to an upper connecting mechanism 112a-112f in a manner that can provide at least two degrees of movement. Each lower attachment mechanism 110 is also mounted to a lower connecting mechanism 114a-114f in a manner that can provide at least two degrees of movement. The upper connecting mechanisms 112 are slidably (or otherwise moveably) mounted on the first base element 102, and the lower connecting mechanism 114 are slidably (or otherwise moveably) mounted on the second base element 104, using carriages or a similar structure that permits sliding of the mechanisms 112, 114 around the rings, but not for the mechanisms 112, 114 to be removed from the rings when pressure is applied using the struts 106. It should be noted that in many embodiments, all of the upper and lower connecting mechanisms 112, 114 are moveably connected to the tracks/base elements 102, 104; however, in other embodiments less than all of the connecting members 112, 114 are moveably connected to the base elements 102, 104, and are instead fixedly connected thereto. Accordingly, the movements of the struts 106 described herein may be made to all of the strut 106 ends, or only to some of them.

In a preferred embodiment, the first base element 102 is a substantially circular ring for placing around a patient's leg. The first base element 102 may be provided in various shapes and sizes, dependent upon the patient's frame and/or the afflicted area to be treated. For example, base elements employed herein may not necessarily be completely enclosed, such as comprising a semi- or partial-circular shape, or even just a partial linearly-shaped frame, or even an angled frame. The first base element 102 further includes a plurality of apertures 116 therethrough. The apertures 116 are sized, shaped and spaced apart for securing transfixation screws, wires or pins, etc., to be secured thereto with typical fixator clamps or the like, as will be apparent to those skilled in the art for securing the first base element 102 to a patient's bone. In addition, the apertures 116 provide places for the affixing of additional struts or other support components designed to help hold the relative positions of the first and second base elements 102, 104. In such embodiments, the apertures 116 may also provide locations for attaching a third base element (not illustrated) to either the first or second base elements 102, 104.

The first base element 102 may also include one or more tracks 118 for use with the sliding mechanisms 112 disclosed above. In the illustrated embodiment of FIG. 1, two tracks 118a, 118b are present on the upper base element 102. The track(s) 118 may be integral to the first base element 102 or may be a separate component attachable to the first base element 102. In embodiments employing attachable tracks 118, the tracks 118 (and any necessary strut 106 connecting components) may beneficially be retrofitted to ring/base elements not having tracks. Accordingly, the advantages provided by the principles of the present disclosure may be extended to existing fixator designs.

The tracks 118 allow for circumferential movement of the upper connecting mechanism 112 around the first base element 102. However, in embodiments where either or both of the base elements 102, 104 are not circular or otherwise fully enclosed, the track(s) may 118 simply follow the shape and extent of the base element(s) employed. Thus, although circular base elements 102, 104 with circumscribing tracks 118 are discussed herein, it should be understood that no limitation to such a specific design and structure is intended. Further, while the tracks 118 are illustrated with a specific groove structure, the tracks 118 may be comprised of any mechanism which allows for the connection and the movement of the upper connecting mechanism 112 around the first base element 102. In addition, the tracks 118 may include teeth configured to engage one or more gears associated with the struts, as described in further detail below. While in a preferred embodiment, the first base element 102 includes first and second tracks 118a, 118b, more or less tracks are also within the broad coverage of the present disclosure.

Also in a preferred embodiment, the second base element 104 is also a substantially circular ring for placing around a patient's leg. Like the first base element 102 in such an embodiment, the second base element 104 may be various shapes and sizes, dependent upon the patient's frame. The second base element 104 further includes a plurality of apertures 120 therethrough. The apertures 120 are sized, shaped and spaced apart for securing transfixation screws, wires or pins, additional base elements, etc., to be secured thereto with typical fixator clamps or the like as will be apparent to those skilled in the art for securing the second base element 104 to a patient's bone. The second base element 104 also includes one or more tracks 118. The track 118 may again be integral to the second base element 104 or may be a separate component attachable to the second base element 104. The track 118 allows for circumferential movement of the lower connecting mechanism 114 around the second base element 104. While a track 118 is shown, the track 118 may be any mechanism which allows for the movement of the lower connecting mechanism 114 around the second base element 104. In a preferred embodiment, the second base element 104 further includes a first track 118a and a second track 118b.

In a preferred embodiment, there are six struts 106, being substantially identical. Of course, in other configurations, there may be a fewer or greater number of struts 106. For example, in embodiments where the first and second base elements 102, 104 comprise square shapes or octagon shapes, the number of struts 106 (or pairs of struts 106) may correspond to the sides of such shapes. The struts 106 may be a solid rod having a fixed length, although adjustable length struts may be employed for one or more of the struts 106. The length will be dependent, at least partially, upon the length of the patient's bone, as well as the course of therapy for the affliction of that bone. In the present disclosure, when describing only one strut 106 and its corresponding upper attachment mechanism 108 and lower attachment mechanism 110, the description would be true for all struts 106. On a first end of the strut 106 is the upper attachment mechanism 108, on the opposite end of the strut 106 is the lower attachment mechanism 110. In some embodiments, the upper attachment mechanism 108 and the lower attachment mechanism 110 are substantially identical.

The upper attachment mechanism 108 may be any mechanism capable of allowing a variable range of motion between the strut 106 and the first base element 102, via the upper connecting mechanism 112. In the illustrated embodiment, the upper attachment mechanism 108 is a passive ball-and-socket joint. However, in other embodiments, the upper attachment mechanism 108 may be a universal joint, a heim joint, a johnny joint, or any joint known by one skilled in the art or even later developed that would allow the range of motion described herein. In some embodiments, the upper attachment mechanism 108 is connected to the end of the strut 106 by means known to one skilled in the art, for example, it may be welded. In other embodiments, the upper attachment mechanism 108 may include a threaded extension threaded into the end of the strut 106. Alternatively, the upper attachment mechanism 108 may include a different type of extension element that is otherwise connected to the end of the strut 106. Moreover, that means of connection between such an extension and the strut 106 may be adjustable, thus adjusting the relative position of the upper attachment mechanism 108 with respect to the strut 106, and thereby adjusting the distance between the first and second base elements 102, 104 along the length of that strut 106. In still other embodiments, the upper attachment mechanism 108 may be an integral part of the strut 106.

The upper attachment mechanism 108 is also connected to the upper connecting mechanism 112. As described above with regard to the upper attachment's 108 connection to the strut 106, the upper attachment 108 may also be connected to the upper connecting mechanism 112 in a variety of ways. For example, the upper attachment mechanism 108 may be welded to the upper connecting mechanism 112, or it may be threadedly attached to the upper connecting mechanism 112.

As mentioned above, and as illustrated in FIG. 1, the upper connecting mechanism 112 is connected to the first base element 102 via one or more tracks 118. While describing only one upper connecting mechanism 112 and its connection to the track(s) 118, the description would be true for all upper connecting mechanisms 112. The upper connecting mechanism 112 is preferably a carriage that is slidably connected to the track 118. As used herein, the term "carriage" is broadly defined to include any component designed to carry something on or along something else. For example, the connecting mechanisms 112, 114 comprise carriages configured to carry the ends of the struts 106 along the tracks 118.

Dependent upon the placement of the other struts 106, the upper connecting mechanism 112 is connected to either the first track 118a or the second track 118b, for a two-track system. Furthermore, as illustrated in FIG. 1, the first rack 118a is provided as a raised structure configured to be received in a similarly sized slot or groove in one or more of the upper connecting mechanisms 112. Conversely, the second track 118b is illustrated as a slot or groove configured to received the upper connecting mechanism(s) 112 therein. In an advantageous embodiment, the grooves in either the upper connecting mechanism(s) 112 or the track(s) is provided as a dove tail, which beneficially allows the upper connecting mechanism(s) 112 to slide (or otherwise move, in other embodiments) along the track 118 (and around the first base element 102), while securely maintaining the upper connecting mechanism(s) 112 within the groove. Of course, however, the grooves, whether in the track 118 or the upper connecting mechanism(s) 112 can have any shape providing the relative movement described herein. FIGS. 3a-3d illustrate cross-sectional views of some exemplary embodiments of carriage shapes for use as the connecting mechanisms 112a-112d (and/or 114a-114d). Of course, depending on the configuration and shape of the carriage(s) used, the track(s) for such carriage(s) would have a corresponding mating cross-sectional shape.

By connecting the upper attachment mechanism 108 to the upper connecting mechanism 112 and not directly to the first base element 102, the strut 106 is capable of an unlimited set of orientations with six degrees of motion of the first base element 102. Additionally, although a carriage-type upper connecting mechanism 112 is illustrated in FIG. 1, the upper connecting mechanism 112 may be any mechanism which allows the upper attachment mechanism 108 to be moved in a circumferential path via the track 118 around the first base element 102.

Figure 4:
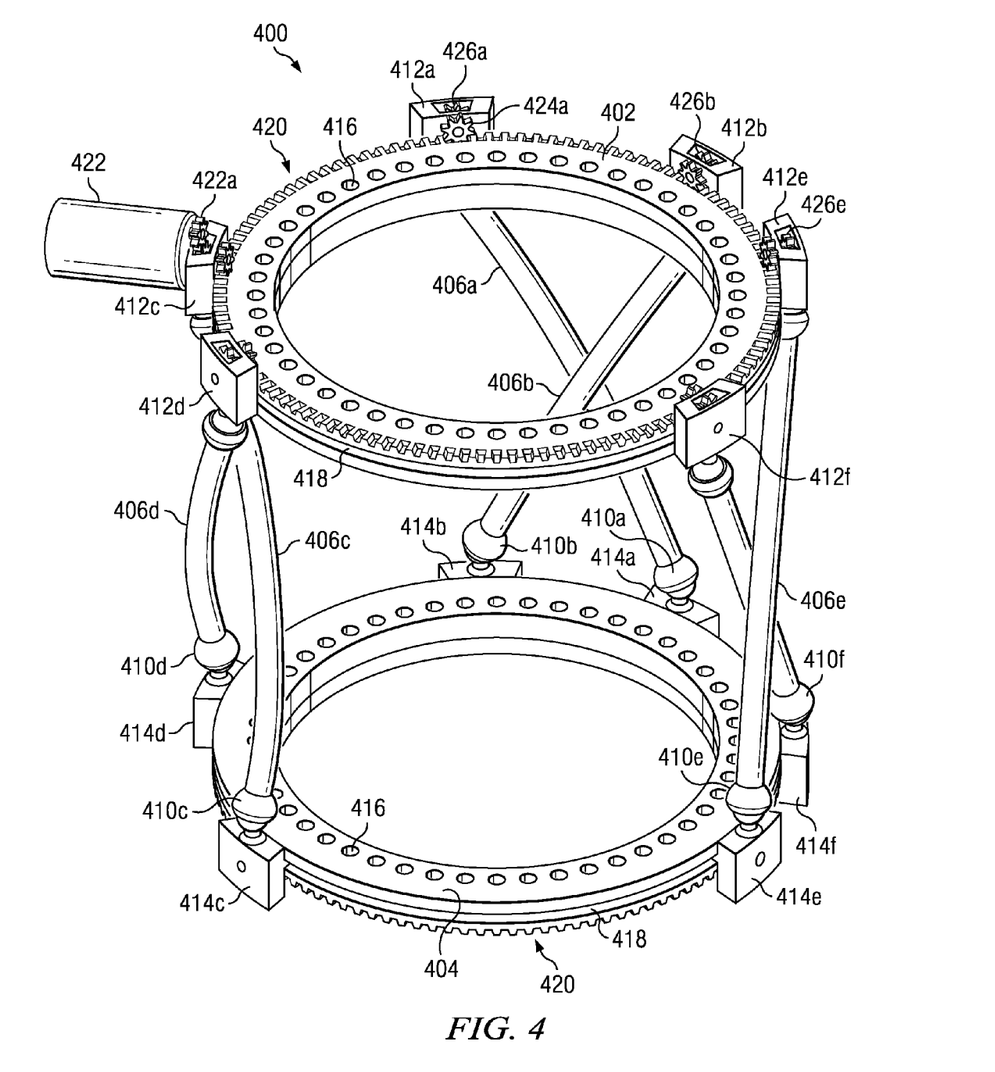
FIG. 4 is a perspective view of yet another embodiment of an orthopedic fixation system of the present invention.
Figure 4A:
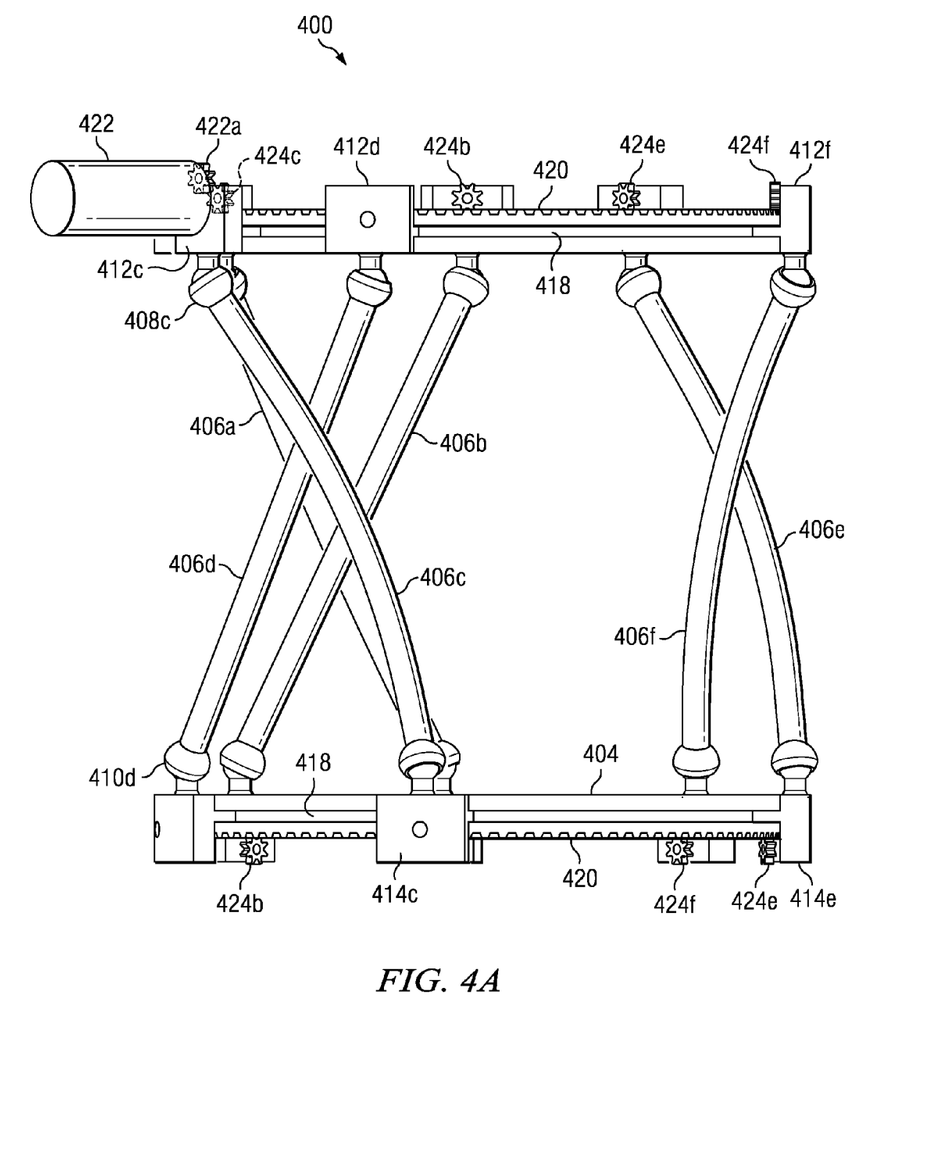
FIG. 4A is a side view of the embodiment of the orthopedic fixation system of FIG. 4.

The upper connecting mechanism 112 translates along the first base element 102 via the one or more tracks 118. In some embodiments, the upper connecting mechanism 112 and/or the track 118 may include a drive system to gradually and controllably re-orient the first base element 102. For example, the carriages comprising the upper connecting mechanisms 112 (and/or the lower connecting mechanisms 114 discussed below) could include one or more gears therein configured to engage teeth located on or within the tracks 118. The drive system could then comprise one or more points through which the gear(s) in the carriages are turned in order to move the carriages along the tracks 118. FIGS. 4 and 4A, described below, illustrate such an embodiment. In other embodiments, a worm gear-based drive system may be employed, where the carriage(s) include the screw of the system, and the track(s) 118 again include teeth to corresponding to drive screw.

The drive system could also include a locking mechanism that would hold the upper connecting mechanism 112 in a static position until intentionally moved to reposition the struts 106 and thus re-orient the first base element 102. The drive system may be, for example, a rack and pinion system, and may include one or more non-moving gears on the carriage(s) configured to engage the teeth on the track(s) 118 for locking, and disengage the teeth for unlocking, the movement of the carriage(s). In other embodiments, a simple screw (e.g., a thumb screw, set screw, or the like) passing through the carriage(s) and contacting the track(s) 118 may provide the locking mechanism. In embodiments employing a worm gear drive system, stopping the turning of the screw in the carriage (s) when adjustments are finished may be enough to prevent further movement of the carriage(s), and thus provide the locking mechanism.

In some embodiments, the drive system may be separate from the fixator device 100, and removably attached to the fixator device 100 to drive the locations of the carriages comprising the upper connecting mechanisms 112. However, the drive system may still be manipulated by medical personnel to position or reposition the upper connecting mechanisms 112 with respect to the first base element 102. In most embodiments, regardless of drive system, the upper connecting mechanisms 112 are capable of moving independently from one another, accordingly providing great degree of movement of the first base element 102 with respect to the second base element 104. However, in still other embodiments, two or more struts 106 may have their ends that are proximate either of the base elements 102, 104 connected to a single connecting mechanism 112. In such embodiments, the other ends of those end-connected struts 106 may still be independent from one another.

Similar to the upper attachment mechanisms 108 described above, the lower attachment mechanisms 110 may be any mechanism capable of allowing a variable range of motion between the strut 106 and the second base element 104, via the lower connecting mechanisms 114. In the illustrated embodiment, the lower attachment mechanism 110 is also a passive ball-and-socket joint. However, in other embodiments, the lower attachment mechanism 110 may be a universal joint, a heim joint, a johnny joint, or any joint known by one skilled in the art or even later developed that would allow the range of motion described herein. In some embodiments, the lower attachment mechanism 110 is connected to the end of the strut 106 by means known to one skilled in the art, such as the welding described above. In other embodiments, the lower attachment mechanism 110 may include a threaded extension threaded into the end of the strut 106 opposite to the upper attachment mechanism 108. Alternatively, the lower attachment mechanism 110 may include a different type of extension element that is otherwise connected to the end of the strut 106. Moreover, as with the upper attachment mechanism 108, that means of connection between such an extension and the strut 106 may be adjustable, thus adjusting the relative position of the lower attachment mechanism 110 with respect to the strut 106, and thereby adjusting the distance between the first and second base elements 102, 104 along the length of that strut 106. In still other embodiments, lower attachment mechanism 110 may simply be an integral part of the strut 106.

The lower connecting mechanism 114 is connected to the second base element 104 via one or more tracks 118. While describing only one lower connecting mechanism 114 and its connection to the track(s) 118, the description would be true for all lower connecting mechanisms 114. Moreover, it is again emphasized that not all of the lower connecting mechanisms 114 are necessarily moveably connected to the second base element 104, and thus one or more may be fixed to the base element 104. The lower connecting mechanism 114 is also preferably a carriage that is slidably (or otherwise moveably) connected to the track 118 on the lower base element 104. Dependent upon the placement of the other struts 106, the lower connecting mechanism 114 is connected to either the first track 118a or the second track 118b, for a two-track system, such as that illustrated in FIG. 1. As also illustrated in FIG. 1, the second rack 118b on the second base element 104 is the one provided as a raised structure configured to be received in a similarly sized slot or groove in one or more of the lower connecting mechanism 114. Conversely, the first track 118a is illustrated as a slot or groove configured to received the lower connecting mechanism(s) 114 therein. In an advantageous embodiment, the grooves in either the lower connecting mechanism(s) 114 or the track(s) on the lower base element 104 are again provided as a dove tail, which beneficially allows the lower connecting mechanism(s) 114 to slide along the track 118 (and around the second base element 104), while securely maintaining the lower connecting mechanism(s) 114 within the groove. Of course, however, the grooves, whether in the track 118 or the lower connecting mechanism(s) 114 can have any shape providing the relative secure connection and movement described herein.

By connecting the lower attachment mechanism 110 to the lower connecting mechanism 114 and not directly to the second base element 104, the strut 106 is capable of an unlimited set of orientations with six degrees of motion of the second base element 104. Additionally, although a specific structure is illustrated for the lower connecting mechanism 114 is illustrated in FIG. 1, the lower connecting mechanism 114 may be any mechanism which allows the lower attachment mechanism 110 to be moved along the track 118 of the second base element 102, or may be fixed with respect to the lower base element 104 for those strut ends not intended to move along the track.

The lower connecting mechanism 114 translates along the second base element 104 via the one or more tracks 118. In some embodiments, the lower connecting mechanism 114 and/or the track 118 may include a drive system to gradually and controllably re-orient the second base element 104. This drive system may be the same or different from a drive system incorporated or employed with the upper connecting mechanisms 112 and the upper track 118. As before, the drive system could also include a locking mechanism that would hold the lower connecting mechanism 114 in a static position until intentionally moved to reposition the struts 106 and thus re-orient the second base element 104. The system may be, for example, a rack and pinion system or a worm gear system, or any other beneficial drive system capable for use herein. In other embodiments, as discussed above, the drive system may be separate from the fixator device 100, and removably attached to the fixator device 100 to drive the locations of the lower connecting mechanisms 114 as well. Still further, the drive system may simply be manipulation by medical personnel to position or reposition the lower connecting mechanisms 114 with respect to the second base element 104, and thus not include any mechanical driving parts. In all embodiments, regardless of drive system, some or all of the lower connecting mechanisms 114 may also capable of moving independently from one another, accordingly providing great degree of movement of the second base element 104 with respect to the first base element 102. As with the upper connecting mechanisms 112, however, one or more may be fixedly connected to the lower base element 104.

The orthopedic fixation system 100 constructed in accordance with the disclosed principles is used to position a displaced bone or other bone-related use as described above. When used to position a displaced bone or similar task, the first base element 102 and the second base element 104 are separated some distance by the struts 106. Depending on the therapy proposed, the struts 106 are adjusted using a combination of moving the struts 106 and either the upper attachment mechanism(s) 18/upper connecting mechanism(s) 112, or the lower attachment mechanism(s) 110/lower connecting mechanism(s) 114 or any combination of these components. Notably, not all of the struts 106 necessarily need adjustment, either along the track(s) 118 or along their lengths, if adjustable length struts 106 are employed. The upper attachment mechanism(s) 18 and lower attachment mechanism(s) 110 mounted with at least two degrees of movement allow for six degrees of freedom when combined with the sliding/movement of the upper connecting mechanism(s) 112 and lower connecting mechanism(s) 114 with respect to the first and second base elements 102, 104.

If a pair of struts 106 are configured in a cross arrangement (as shown in both FIG. 1 and FIG. 2), the vertical height can be increased by drawing one or more of the upper connecting mechanisms 112 of the struts 106 together (or the lower connecting mechanisms 114, or both). To bring such components together, one or more of the upper and/or lower connecting mechanism(s) 112/114 are loosened/unlocked from their respective base element 102, 104, and then slid/moved along their respective track 118 to the desired position(s). The mechanism(s) can then be locked in their new position(s). As mentioned above, the sliding/moving of one or more of these mechanisms 112/114 may be accomplished by a drive system, however, such a system is not required. Similarly, when a pair of struts 106 are configured in the illustrated crossing arrangement, the vertical height can be decreased by pushing apart the upper connecting mechanisms 112 of the struts 106 (or the lower connecting mechanisms 114, or both). Again, this can be accomplished by unlocking or otherwise loosening the mechanisms 112/114 from their respective base elements 102/104, and sliding/moving the mechanism(s) 112/114 along their respective track(s), and then locking the one or more repositioned mechanism(s) 112/114 in their new position(s). Changing the positions of the upper connecting mechanisms 112 and/or the lower connecting mechanisms 114 along with the ability of the upper attachment mechanisms 108 and the lower attachment mechanisms to provide at least two degrees of movement 110 provides flexibility to the positioning of the first base element 102 and the second base element 104 with respect to one another.

Figure 2:
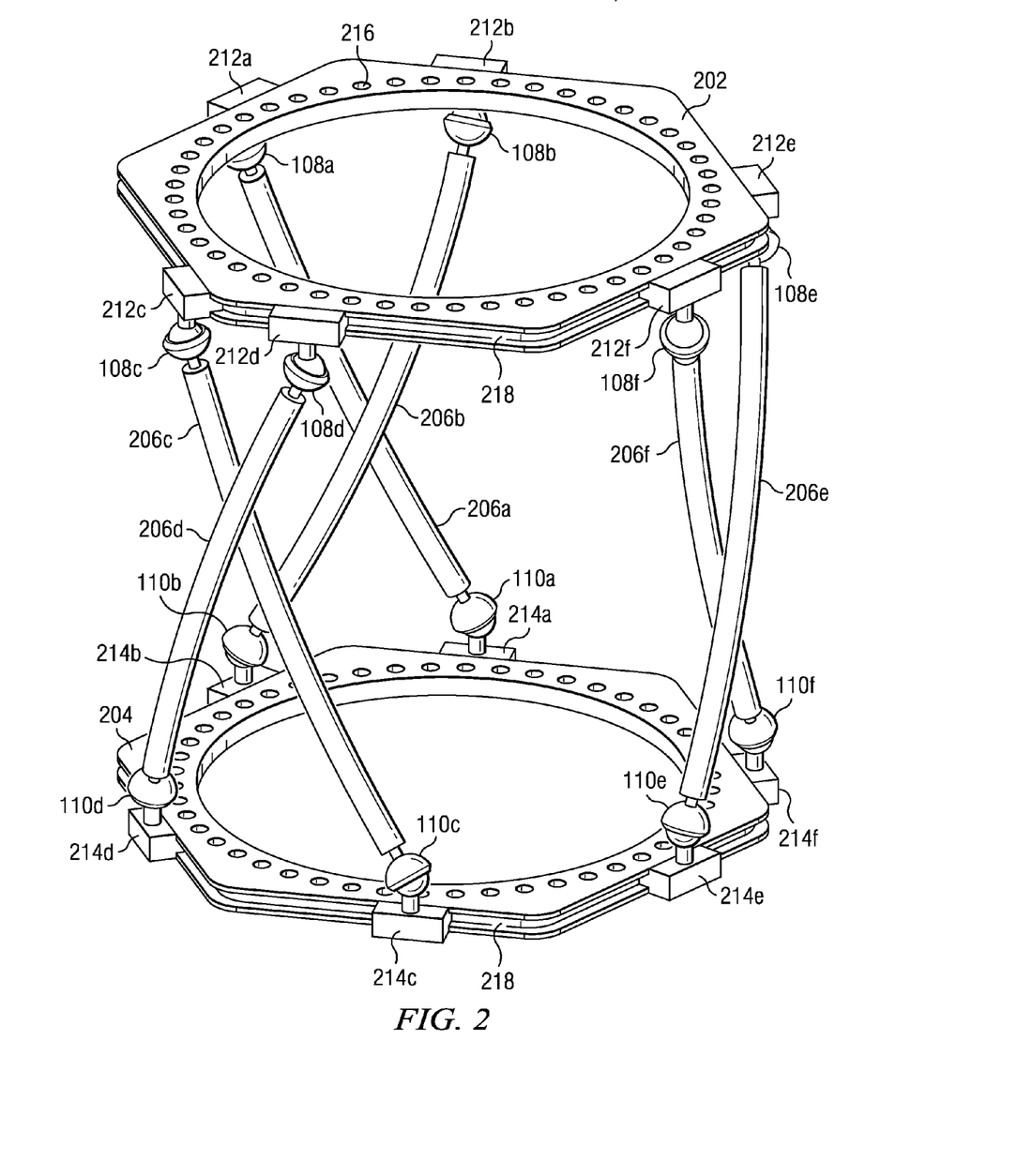
FIG. 2 is a perspective view of an alternate embodiment of an orthopedic fixation system of the present invention.
Figure 3A:
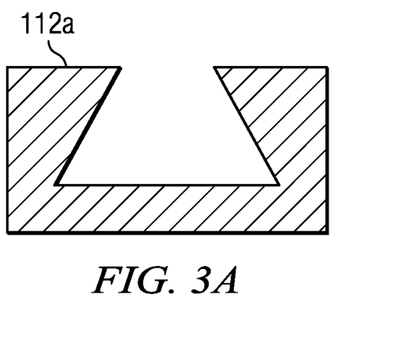
FIGS. 3a-3d are cross-sectional views of exemplary embodiments of carriage shapes for use as connecting mechanism disclosed herein.
Figure 3B:
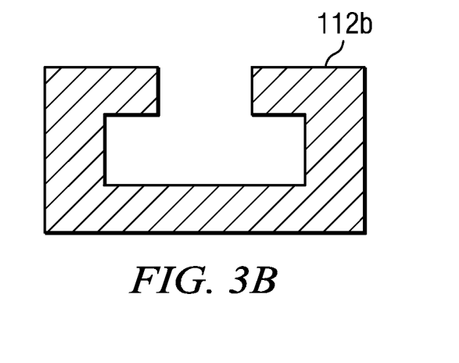
Figure 3C:
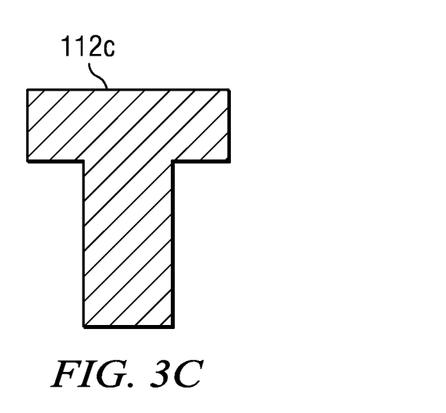
Figure 3D:
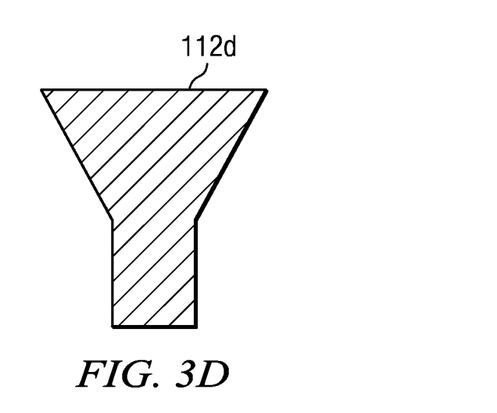

Turning now to FIG. 2, illustrated is an alternate embodiment of an orthopedic fixation system 200 constructed in accordance with the disclosed principles. This embodiment of the disclosed fixation system 200 has variations from the orthopedic fixation system 100 illustrated in FIG. 1. That being said, designator numbers and their accompanying descriptions for parts that are the same or similar between the two embodiments will be the same as detailed in the description of FIG. 1, and thus those descriptions will not be detailed again with reference to FIG. 2.

One of the distinctions between the two embodiments is the that the alternate embodiment of FIG. 2 includes a first base element 202 and a second base element 204 that has a hexagonal ring with a circular aperture therethrough. The first base element 202 includes a single track 118, and the second base element 204 includes just a single track 118 as well. By providing the first and second base elements 202, 204 with a hexagonal shape, use of this embodiment of the fixator device 200 can be simplified since the sliding movement of each of the upper and lower connecting mechanisms 212, 214 is limited to one of the "sides" of the hexagonal shape of the base elements 202, 204. Moreover, because the sliding movement of the upper and lower connecting mechanisms 212, 214 along their respective base elements is linear rather than the circular movement seen in the embodiment of FIG. 1, the manufacture of the raised portions or grooves of the connecting mechanisms 212, 214 and their corresponding track 218 grooves or raised portions may be simplified since all of the manufactured surfaces may be rectilinear. When compared with machining or grinding precision surfaces have mating curved portions, the use of rectilinear mating surfaces can substantially decrease manufacturing costs for the ring elements 202, 204 and thus the overall fixator device 200. Of course, in embodiments where the connecting mechanisms 212, 214 do not actually slide on the tracks 218, and instead roll for example on gears, the same precision may be present for such curved mating components.

Another difference between the embodiments of FIG. 1 and FIG. 2 is that the base elements 202, 204 of the fixator device 200 in FIG. 2 includes large number of apertures 216 formed through the base elements 202, 204. The apertures 216 in this embodiment may again be sized, shaped and spaced apart for securing transfixation screws, wires or pins, etc., to be secured thereto with typical fixator clamps or the like, as will be apparent to those skilled in the art for securing the first and second base elements 202, 204 to a patient's bone. In addition, the large number of apertures 216 in this embodiment provides numerous places for the affixing of additional struts or other support components designed to help hold the relative positions of the first and second base elements 202, 204.

Yet another difference between the embodiments of FIG. 1 and FIG. 2 is that the struts 206 used in the fixator 200 of FIG. 2 each have a bowed configuration along their lengths. More specifically, each strut 206 in a pair of struts 206 is bowed opposite to the other strut 206 in that pair. Therefore, as illustrated, when a single track 118 is used on each base element 202, 204, the pairs of struts 206 are bowed with respect to each other to prevent the struts 206 in a given pair from contacting each other. In embodiments such as that illustrated in FIG. 1, two tracks along one or both ring elements 202, 204 may be used to help prevent pairs of struts 106 from contacting each other when being positioned. That same goal may be accomplished when only a single track 218 is used for one or both ring elements 202, 204, such as the embodiment in FIG. 2. This approach simplifies the design and construction of the base elements 202, 204 since only one track 218 needs to be formed in the base element(s) 202, 204.

Moreover, this embodiment may be advantageous since the upper connecting mechanisms 212 for all of the struts 206, or all of the lower connecting elements 214 for the struts 206, may be manufactured the same since they share the same track. This allows the upper components of the struts 206 to be interchangeable with other upper strut components. Even further, if the track 218 in both the first and second base elements 202, 204 are manufactured the same, then all of the upper and lower connecting mechanisms 212, 214 may be manufactured the same. This would allow entire struts 206 to be interchangeable, including interchanging upper and lower connecting mechanisms 212, 214, thus further accentuating interchangeability of components for the fixator device 200, as well as simplifying the manufacturing process to a single strut 206 with a single upper or lower connecting mechanism 212, 214.

Yet another embodiment of an orthopedic fixation system constructed according to the disclosed principles is shown in FIGS. 4 and 4A. FIG. 4 provides a perspective view of this alternative embodiment, while FIG. 4A provides a side view of the fixation system of FIG. 4. Looking at these figures together, the orthopedic fixator device or system in this embodiment is identified by the numeral 400.

The fixation system 400 again includes a first base element 402 and a second base element 404. As with other embodiments, the first and second base elements 402, 404 also include a plurality of apertures 416 therethrough, which can be sized, shaped and spaced apart for securing transfixation screws, other fixator frames/rings, wires or pins, etc., to be secured thereto with typical fixator clamps or the like. The first base element 402 and the second base element 404 are also again spaced apart by a plurality of struts 406a-406f. Although six struts 406 of substantially equal length are illustrated, the device is not limited to specifically six struts 406, nor is there any limitation to the use of all equal length struts 406. The base elements 402, 404 in this embodiment are provided as enclosed rings with a substantially circular shape. Of course as with other embodiments, either or both of the base elements 402, 404 may comprise only partially enclosed fixator elements, such as only a partial circular structure or an angular frame, or even simply a linear structure or a frame with both linear and curved portions. Also in this embodiment, six struts 406 are again illustrated. These struts 406 are shown substantially identical to one another in both length and shape. As before, however, in other configurations there may be a fewer or a greater number of struts 406. In addition, some or all of the struts 406 may comprise a solid rod having a fixed length or may be adjustable along their lengths.

Struts 406 again include an upper attachment mechanism 408a-408f and a lower attachment mechanism 410a-410f. Also as before, the upper and lower attachment mechanisms 408, 410 provide for at least two degrees of movement. The upper and lower attachment mechanisms 408, 410 may be any mechanism capable of allowing a variable range of motion between a strut 406 and a base element 402, 404. In the illustrated embodiment, the upper and lower attachment mechanisms 408, 410 are provided as passive ball-and-socket joints. However, some of the attachment mechanisms 408, 410 may be different from others.

Each upper attachment mechanism 408 is mounted to an upper connecting mechanism 412a-412f, and each lower attachment mechanism 410 is mounted to a lower connecting mechanism 414a-414f. The upper connecting mechanisms 412 are slidably mounted on the first base element 402, and the lower connecting mechanism 414 are slidably mounted on the second base element 404, using carriages that permits sliding of the mechanisms 412, 414 around the rings 402, 404, but not for the mechanisms 412, 414 to be removed from the rings 402, 404 when pressure is applied using the struts 406. In some embodiments, less than all of the connecting members 412, 414 are moveably connected to the base elements 402, 404, and are instead fixedly connected thereto. Accordingly, the movements of the struts 406 described herein may be made to all of the strut 406 ends, or only to some of them.

The first and second base elements 402, 404 also include a single track 418 each for use with the sliding mechanisms 412. The tracks 418 allow for circumferential movement of the connecting mechanisms 412, 414 around the base elements 402. While the tracks 418 are illustrated with a specific groove structure, the tracks 418 may be comprised of any mechanism which allows for the connection and the movement of the connecting mechanisms 412, 414 around the base elements 402, 404.

In addition, in this embodiment, the fixator system 400 includes a drive system, which includes a drive motor 422. Such a drive system may be employed with a fixator device 400 according to the disclosed principles to gradually and controllably re-orient the base elements 402, 404. More specifically, one or more of the connecting mechanisms 412, 414 can be translated along the tracks 418 to a desired position. To accomplish this in the illustrated embodiment, the tracks 418 include teeth 420 configured to engage one or more gears 424a-424f associated with the connecting mechanisms 412a-412f, 414a-414f a the ends of the struts 406a-406-f. The carriages comprising the connecting mechanisms 412, 414 include one or more gears 424 therein configured to engage the teeth 420 located on or within the tracks 418. The carriages 412, 414 could comprise one or more points through which the drive motor 422 and its drive gear 422a engage and turn the gears in the carriages 412, 414 in order to move the carriages 412, 414 along the tracks 418. This allows the moveable ones of the connecting mechanisms 412, 414 to move independently from one another. Of course, as discussed above, FIG. 4 provides only an exemplary embodiment of a drive system in accordance with the disclosed principles, and other types of drive system and related techniques for drive the positions of the struts 406 are also within the broad scope of the present disclosure. Also, although the drive system for the two base elements 402, 404 in FIG. 4 are the same, the base elements 402, 404 may include different drive systems.

The drive system could also include a locking mechanism that would hold the connecting mechanisms 412, 414 in a static position until intentionally moved to reposition the struts 406 and thus re-orient the base elements 402, 404 with respect to one another. For example, the gear in the carriages 412, 414 could be planetary or otherwise configured such that the gears 424 configured to engage the teeth 420 would not move along the teeth 420 unless driven by a carriage drive gear 426a-426f. Alternatively, the drive system may include one or more non-moving gears on the carriage 412, 414 configured to engage the teeth 420 on the tracks 418 for locking, and disengage the teeth 420 for unlocking, the movement of the carriages 412, 414. As mentioned above, a simple screw (e.g., a thumb screw, set screw, or the like) passing through the carriages 412, 14 and contacting the tracks 418 may provide the locking mechanism.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

Moreover, while various embodiments of the disclosed principles have been described above, it should be understood that they have been presented by way of example only, and not limitation. Thus, the breadth and scope of the invention(s) should not be limited by any of the above-described exemplary embodiments, but should be defined only in accordance with any claims and their equivalents issuing from this disclosure. Furthermore, the above advantages and features are provided in described embodiments, but shall not limit the application of such issued claims to processes and structures accomplishing any or all of the above advantages.

Additionally, the section headings herein are provided for consistency with the suggestions under 37 C.F.R. 1.77 or otherwise to provide organizational cues. These headings shall not limit or characterize the invention(s) set out in any claims that may issue from this disclosure. Specifically and by way of example, although the headings refer to a "Technical Field," such claims should not be limited by the language chosen under this heading to describe the so-called technical field. Further, a description of a technology in the "Background" is not to be construed as an admission that technology is prior art to any invention(s) in this disclosure. Neither is the "Summary" to be considered as a characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of such claims shall be considered on their own merits in light of this disclosure, but should not be constrained by the headings set forth herein.

What is claimed is:

1. An orthopedic fixation system, comprising:
   (a) a first base element comprising at least one track located on at least a portion of the perimeter of the first base element;
   (b) a second base element comprising at least one track located on at least a portion of the perimeter of the second base element;
   (c) at least six rigid struts spanning between the first base element and the second base element, each of the struts comprising an upper attachment mechanism and a lower attachment mechanism on opposite ends, the attachment mechanisms each capable of at least two degrees of movement;
   (d) at least six upper connecting mechanisms for moveably connecting one or more corresponding ones of the upper attachment mechanisms to the track of the first base element; and
   (e) at least six lower connecting mechanisms for moveably connecting one or more corresponding ones of the lower attachment mechanisms to the track of the second base element;
   wherein the at least six struts comprise three pairs of two crossed struts.

2. The system of claim 1, wherein one or more of the struts has an adjustable length.

3. The system of claim 1, wherein one or more of the struts has a length unequal to a length of at least one of the others of the struts.

4. The system of claim 1, wherein the struts are bowed along their lengths.

5. The system of claim 4, wherein the system comprises three pairs of two crossed struts, wherein one of each of the pairs of bowed struts is bowed opposite to the other of each of the pairs of bowed struts.

6. The system of claim 1, wherein at least one of the upper attachment mechanisms and lower attachment members comprises a ball-and-socket joint, a universal joint, a johnny joint or a heim joint.

7. The system of claim 1, wherein at least one of the one or more upper connecting mechanism and one or more of the lower connecting members comprises a carriage.

8. The system of claim 7, wherein the carriage is movable by a drive system.

9. The system of claim 8, wherein the drive system is provided within the carriage.

10. The system of claim 1, wherein at least one of the one or more upper connecting mechanism is moveable independently of another of the one or more upper connecting mechanism, and at least one of the one or more lower connecting mechanism is moveable independently of another of the one or more lower connecting mechanism.

11. The system of claim 1, wherein the at least one track on the first base element is located on the outer edge of the first base element.

12. The system of claim 1, wherein there are two tracks on at least one of the first and second base elements.

13. The system of claim 12, wherein a first of the two tracks is located on the outer edge of the base element or elements, and the second of the two tracks is located on face of the base element or elements proximate the perimeter of the base element or elements.

14. The system of claim 1, wherein at least one of the first and second base elements comprises a shape selected from the group consisting of:
 an enclosed circular ring,
 a partial circle,
 an enclosed hexagonal ring,
 an enclosed square ring,
 an enclosed triangular ring,
 a linear frame,
 an angular frame, and
 a partially linear and partially curved frame.

15. The system of claim 1, wherein the one or more upper connecting mechanisms and the one or more lower connecting mechanisms each comprise a locking mechanism for locking the connecting mechanisms to their corresponding tracks.

16. An orthopedic fixation system, comprising:
 (a) an upper ring comprising at least one circumferential track and six upper connecting members which are moveable around the at least one track;
 (b) a lower ring comprising at least one circumferential track and six lower connecting members which are moveable around the at least one track;
 (c) at least six struts, each strut comprising a rigid rod, an upper attachment member having at least two degrees of movement at one end, and a lower attachment member having at least two degrees of movement at an opposing end;
 wherein the at least six struts comprise three pairs of two crossed struts;
 wherein each upper attachment member is connected to a corresponding one of the upper connecting members; and
 wherein each lower attachment member is connected to a corresponding one of the lower connecting members.

17. The system of claim 16, wherein the at least six struts comprise pairs of two crossed struts, wherein one of each of the pairs of struts is bowed opposite to the other of each of the pairs of struts.

18. The system of claim 16, wherein at least one of the upper attachment members and lower attachment members comprises a ball-and-socket joint, a universal joint, a johnny joint or a heim joint.

19. The system of claim 18, wherein at least one of the upper connecting members and at least one of the lower connecting members comprise a carriage.

20. The system of claim 19, wherein the carriages are movable by a drive system.

21. The system of claim 20, wherein the drive system is provided within the carriages.

22. The system of claim 16, wherein at least one of the upper connecting members is moveable independent of another of the one or more upper connecting mechanism, and at least one of the lower connecting members is moveable independently of another of the one or more lower connecting mechanism.

23. The system of claim 16, wherein at least one of the tracks on the upper ring and the lower ring is located on the outer edge of its corresponding ring.

24. The system of claim 16, wherein at least one of the upper and lower rings comprises a shape selected from the group consisting of:
 an enclosed circular ring,
 an enclosed hexagonal ring,
 an enclosed square ring, and
 an enclosed triangular ring.

25. The system of claim 16, wherein the upper connecting members and the lower connecting members each comprise a locking mechanism for locking the connecting members to their corresponding tracks.

26. The system of claim 16, wherein one or more of the struts have a fixed length with respect to at least one other of the one or more struts.

27. An orthopedic fixation system, comprising:
 (a) an upper ring comprising a first circumferential track having at least three first upper connecting members, one or more of which are moveable around the first track, and a second circumferential track having at least three second upper connecting members, one or more of which are moveable around the second track;
 (b) a lower ring comprising a third circumferential track having at least three first lower connecting members, one or more of which are moveable around the third track, and a fourth circumferential track having at least three second lower connecting members, one or more of which are moveable around the fourth track;
 (c) at least six struts, each strut comprising a rigid rod, an upper attachment member having at least two degrees of movement at one end, and a lower attachment member having at least two degrees of movement at an opposing end;
 wherein the at least six struts comprise three pairs of two crossed struts;

wherein the at least three upper attachment members on the first track are connected to corresponding ones of the at least three first upper connecting members;

wherein the at least three upper attachment members on the second track are connected to corresponding ones of the at least three second upper connecting members;

wherein the at least three lower attachment members on the third track are connected to corresponding ones of the at least three first lower connecting members; and wherein the at least three lower attachment members on the fourth track are connected to corresponding ones of the at least three second lower connecting members.

28. The system of claim 27, wherein at least one of the struts has an adjustable length.

29. The system of claim 27, wherein at least one of the upper attachment members and lower attachment members comprises a ball-and-socket joint, a universal joint, a johnny joint or a heim joint.

30. The system of claim 27, wherein moveable ones of the upper connecting members and the lower connecting members each comprise a carriage.

31. The system of claim 30, wherein the carriages are movable by a drive system.

32. The system of claim 31, wherein the drive system is in the carriages.

33. The system of claim 27, wherein all of the upper connecting members are moveable independently of each other, and all of the lower connecting members are moveable independently of each other.

34. The system of claim 27, wherein the first track is located on the outer edge of the upper ring and the second track is located on a lower surface of the upper ring proximate the perimeter of the upper ring.

35. The system of claim 34, wherein the third track is located on the outer edge of the lower ring and the second track is located on an upper surface of the lower ring proximate the perimeter of the lower ring.

36. The system of claim 27, wherein at least one of the upper and lower rings comprises a shape selected from the group consisting of:
an enclosed circular ring,
an enclosed hexagonal ring,
an enclosed square ring, and
an enclosed triangular ring.

37. The system of claim 27, wherein moveable ones of the first and second upper connecting members and the first and second lower connecting members each comprise a locking mechanism for locking the connecting members to their corresponding tracks.

38. An orthopedic fixation system, comprising:
(a) a first base element and a second base element, at least one of the first or second base elements comprising at least one track located on at least a portion of the perimeter of the first base element;
(b) a plurality of rigid struts spanning between the first and second base elements, each of the struts comprising an upper attachment mechanism and a lower attachment mechanism on opposite ends, the attachment mechanisms each capable of at least two degrees of movement;
(c) one or more upper connecting mechanisms for connecting one or more corresponding ones of the upper attachment mechanisms to the at least one track of the first base element, if present;
(d) one or more lower connecting mechanisms for connecting one or more corresponding ones of the lower attachment mechanisms to the at least one track of the second base element, if present;
wherein at least one of the upper or lower connecting mechanisms is moveable along a corresponding one of the at least one track; and
wherein the plurality of rigid struts comprise pairs of crossed struts.

39. The system of claim 38, wherein one or more of the plurality of struts has an adjustable length.

40. The system of claim 38, wherein one or more of the plurality of struts has a length unequal to a length of at least one of the others of the plurality of struts.

41. The system of claim 38, wherein at least one of the plurality of struts are bowed along its length.

42. The system of claim 41, wherein the system comprises at least one pair of struts crossed struts, wherein one of the struts in a pair is bowed opposite to the other of the struts in that pair.

43. The system of claim 38, wherein at least one of the upper attachment mechanisms and lower attachment members comprises a ball-and-socket joint, a universal joint, a johnny joint or a heim joint.

44. The system of claim 38, wherein at least one of the one or more upper connecting mechanism and one or more of the lower connecting members comprises a carriage.

45. The system of claim 44, wherein the carriage is movable by a drive system.

46. The system of claim 45, wherein the drive system is provided within the carriage.

47. The system of claim 38, wherein the at least one track on the first or second base element is located on the outer edge of its corresponding base element.

48. The system of claim 38, wherein at least one of the first and second base elements comprises a shape selected from the group consisting of:
an enclosed circular ring,
a partial circle,
an enclosed hexagonal ring,
an enclosed square ring,
an enclosed triangular ring,
a linear frame,
an angular frame, and
a partially linear and partially curved frame.

49. The system of claim 38, wherein the at least one of the moveable upper and lower connecting mechanisms comprises a locking mechanism for locking the connecting mechanism to its corresponding track.

50. The system of claim 38, wherein only one of the first or second base elements comprises one or more tracks, and wherein the one or more connecting mechanisms connected to the base element without a track are non-moveable with respect to that base element.

* * * * *